United States Patent [19]
Fahlvik et al.

[11] 4,111,654
[45] Sep. 5, 1978

[54] AUTOCLAVE APPARATUS AND METHOD FOR STERILIZATION OF ARTICLES

[75] Inventors: Hans Anders Fahlvik, Slöinge; Nils Arne Fahlvik, Getinge, both of Sweden

[73] Assignee: Aktiebolaget Electrolux, Stockholm, Sweden

[21] Appl. No.: 778,385

[22] Filed: Mar. 17, 1977

[30] Foreign Application Priority Data

Mar. 19, 1976 [SE] Sweden .................................. 7603436

[51] Int. Cl.² ........................... A61L 3/00; A61L 3/02
[52] U.S. Cl. ........................................ 422/26; 422/38; 422/112; 422/295
[58] Field of Search ......................... 21/56, 57, 94–98, 21/104

[56] References Cited
U.S. PATENT DOCUMENTS

| 3,093,449 | 6/1963 | Kotarski et al. | 21/94 |
| 3,454,353 | 7/1969 | Rjork | 21/97 |

FOREIGN PATENT DOCUMENTS 899,249 12/1953 Fed. Rep. of Germany .............. 21/94

Primary Examiner—Morris O. Wolk
Assistant Examiner—Bradley R. Garris
Attorney, Agent, or Firm—Alfred E. Miller

[57] ABSTRACT

An apparatus and method for steam sterilizing articles having an inner chamber for receiving said articles and an outer space between the outer wall of the chamber and the inner wall of the chamber. A constant pressure difference is maintained between the chamber and the outer space. This constant pressure difference permits the thermodynamic optimum steam flow to the chamber with a minimum of energy losses.

7 Claims, 2 Drawing Figures

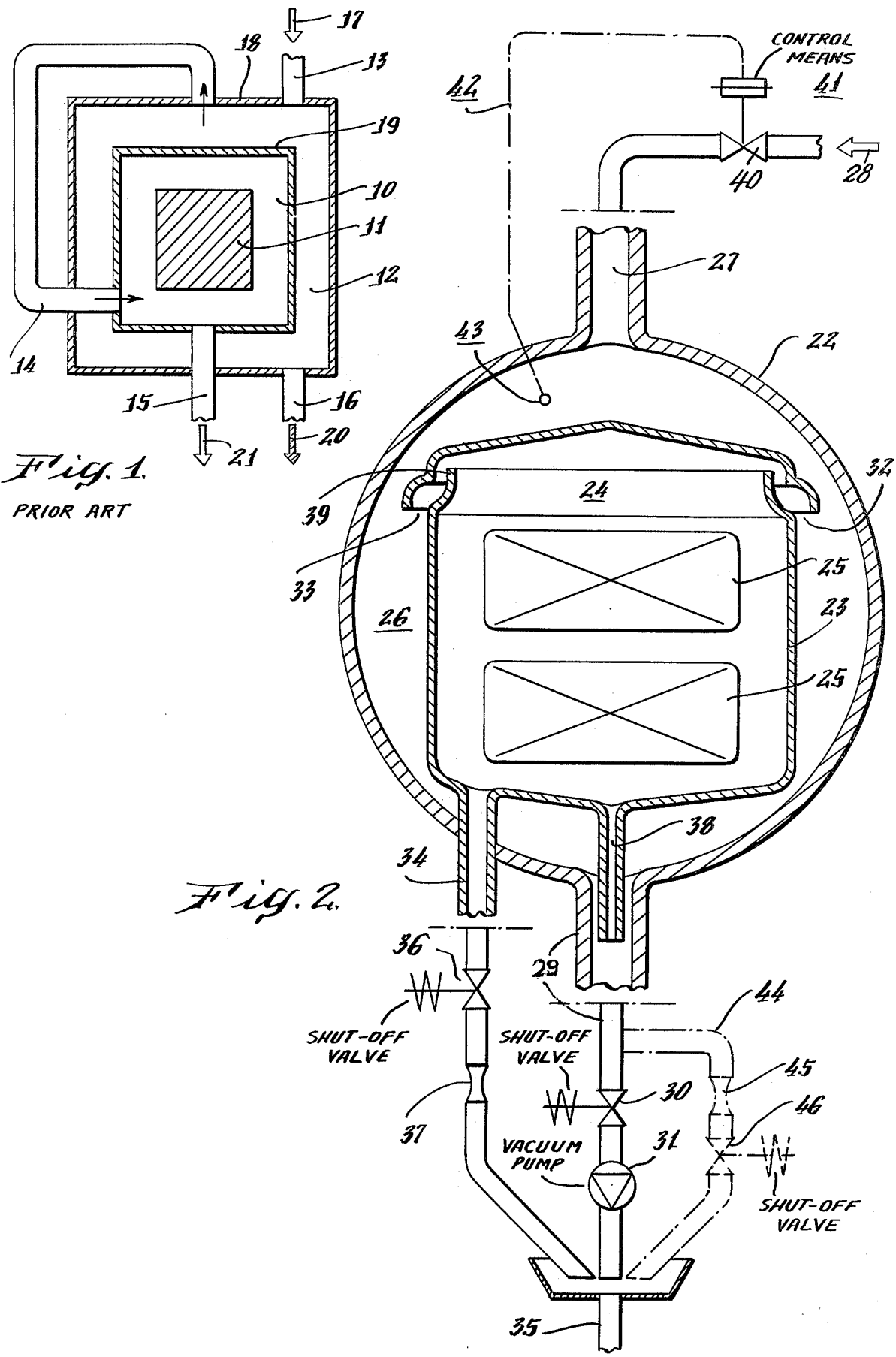

AUTOCLAVE APPARATUS AND METHOD FOR STERILIZATION OF ARTICLES

BACKGROUND OF THE INVENTION

An apparatus and method is known for sterilizing articles or items in an autoclave having steam as a medium and provided with an outer wall of a pressure vessel and an inner wall that is not a pressure vessel but defines a chamber to receive the articles to be sterilized. In this known apparatus, the chamber is surrounded by an outer space between said outer and inner walls. Furthermore, the autoclave has a steam supply conduit connected to the outer space and a connection between the latter space and the chamber. This known autoclave type does not operate satisfactorily since the operating procedure has to be carefully supervised and the results controlled. It is well known that the articles to be treated are not always rendered sterile after treatment and because of this uncertainty the treatment time is extended beyond what should theoretically be necessary to render said articles sterile. It has been found through investigation that the irregular treatment of the articles in the autoclave results since part of the steam supplied to the autoclave is condensed in the space between the chamber and the outer wall and that at least part of the condensate is entrained by the flow of steam being transferred from the space to the chamber. In some cases this flow will hold an amount of condensate greater than the amount formed only by the condensation of steam when the items or articles are heated from room temperature to the desired sterilization temperature. Moreover, it is well-known that the presence of water in or on the articles to be treated obstructs the killing of bacteria and involves a great risk of recontamination of the sterilized material or articles.

In addition to the disadvantage of uncertainty with respect to the result of the sterilization treatment, the above mentioned condensation of steam in the space and in connection with the chamber causes considerable heat losses and consequently extra costs for the sterilization treatment. Furthermore, there will be an additional cost due to prolonged treatment in order to achieve the desired result.

It is an object of the present invention to overcome the disadvantages of the prior construction and achieve both reliable treatment and lower cost for said treatment.

It is another object of the present invention to provide a sterilization treatment in which steam is supplied to an autoclave an an almost constant pressure difference is maintained between the outer space and the chamber, and this result is effective since the connection between the outer space and the chamber is a special design and a quantity of steam is discharged from the chamber. The aforesaid connection is so constructed as to cause a given pressure difference between the outer space and the chamber and further that the chamber has a restricted outlet.

It is an object of the present invention to provide an arrangement whereby the flow velocity of the steam between the outer space and the chamber is so chosen that there will be a minimum of energy losses.

It is another object of the present invention to provide an autoclave in which the risk is eliminated that a steam flow in the connection between the outer space and the chamber forms a constant source of transfer of condensate from said space to said chamber.

In order that the invention will be more clearly understood, it will now be disclosed in greater detail with reference to the accompanying drawings in which:

FIG. 1 is a diagrammatical vertical section of a known autoclave and constituting prior art; and FIG. 2 is a corresponding vertical section of an autoclave constructed in accordance with the teachings of the invention.

DESCRIPTION OF PRIOR ART AND PREFERRED EMBODIMENT

The autoclave shown in FIG. 1 has a chamber 10 in which articles 11 are treated. The chamber 10 is surrounded by an outer space 12 having a steam supply conduit 13. A connection conduit 14 leads to the chamber 10, the latter being provided with a discharge conduit 15. In addition, the space 12 has a discharge conduit 16, by which air and steam condensate are removed. The discharge conduit 15 is connected to a vacuum pump (not shown), which permits effective evacuation of air before steam is introduced into the chamber. The discharge conduit 16 opens to the exterior of the autoclave by means of condensate water drain. The conduits 15 and 16 have valves with control means of a known type and are therefore not illustrated in FIG. 1.

The known autoclave operates in the following manner: Steam is supplied to the autoclave as indicated by the arrow 17 by means of the conduit 13 and flows into the space 12 heating both the casing 18 of the autoclave and its inner wall 19, whereby part of the steam is condensed. Thus, an atmosphere of moist steam and water droplets is obtained in the space 12, and this atmosphere is conducted into the chamber 10 through the conduit 14. The flow velocity of the steam in this conduit is comparatively high so that, on one hand, heat losses will occur because kinetic energy is consumed by means of the steam transport, and, on the other hand, the steam of high velocity will sweep water droplets from the space 12 through the connecting conduit 14 and entrain them with the steam flow into the chamber 10. In the chamber 10, the heat contents of the steam is used during a first stage to heat the articles 11 from room temperature to sterilization temperature, and during a second stage to maintain this sterilization temperature of the articles for a given time. Some heat is also consumed for heating the inner wall 19. Furthermore, from the space 12, condensate is led out through the discharge conduit 16 as shown by the arrow 20. However, if the pressure becomes too high, steam is removed from the chamber 10 by way of the discharge conduit 15, as indicated by the arrow 21.

It should be noted that the presence of condensate in the chamber 10 is a drawback during treatment. How seriously the treatment is affected depends, of course, also on the type of material being treated and how it is packed and charged into the chamber, etc. What is certain, however, is that the treatment would be both more reliable and more inexpensive if the presence of condensate in the chamber 10 could be avoided.

A given quantity of steam with a specified heat content is introduced into the chamber if it is desired to supply a certain amount of heat to the articles to be sterilized. Exterior to the chamber, heat is used to generate steam which is used for heat transport to the articles. Should the velocity of the steam be too low, the heat quantity supplied would be too small, however, should be velocity of the steam to too high, large heat losses would occur in the flow path. On one hand, these losses reduce the degree of efficiency, i.e. the relation between the heat quantity used in the chamber and the available heat quantity. On the other hand, the flow losses, which are kinetic energy, result in considerable condensation of steam. Water droplets are formed and are carried into the chamber with the steam and they form a serious disadvantage since it is desired to avoid unnecessary moistening of the articles in the chamber.

Although a small quantity of water droplets are formed at a medium velocity, it is possible to prevent them from being entrained by the steam flow into the chamber. In autoclaves of current available types, the following details are applicable and important:

(1) About 35 m/s is the lowest velocity which provides a sufficient quantity of steam at normal temperatures and pressures of sterilization, 120°-135° C. and 1.0-2.5 at. gauge.

(2) 60 m/s is the highest velocity that should be used because it provides the best possible heat transport and at the same time negligible flow losses. The thermodynamic optimum velocity of steam flowing into a chamber can be determined when the quantity of heat consumed is the lowest possible for a given kind of sterilization. This velocity has by experimentation proved to be about 50 m/s.

Referring to FIG. 2 which shows the present invention, a casing 22 is illustrated having an inner wall 23 enclosing a chamber 24 in which articles 25 are treated. Between the casing 22 and the inner wall 23 an outer space 26 is formed which has large volume compared to that of the chamber 24, or approximately the same volume. Steam is supplied to the outer space by a conduit 27, as shown by the arrow 28. In the bottom part of the space 26 a discharge conduit 29 is provided with a shut-off valve 30 and a vacuum pump 31.

The inner wall 23 forming the enclosure for the chamber 24 is constructed of relatively thin material and provided with ports 32 and 33 on opposite sides thereof through which steam from the space 26 can flow freely into the chamber 24. The abovementioned ports 32 and 33 may take the form of holes or elongated slots having an area adapted to flow therethrough of steam so that a pressure difference of 0.01-0.02 atmospheres is maintained. It will be noted that chamber 24 has a separate discharge conduit 34 which together with the discharge conduit 29 opens into a common drain 35. Furthermore, a shut-off valve 36 and a throttle 37 are provided in the conduit 34. The bottom of the chamber 24 is provided with an opening which is disposed so that any condensate in the chamber can flow directly into the discharge conduit 29 and out of the chamber, however, only small quantities of steam can penetrate the chamber through the opening 38. The ports 32 and 33 between the space 26 in the chamber 24 have a flow resistance of a special magnitude and are of such a form that the steam flowing through the conduit 27 into the space 26 cannot enter the chamber 26 without a preceding change of direction of movement. Thus, the metal plate of the inner wall 23 is bent outwardly at the upper edge of ports 32 and 33 so that the condensate outside above the port cannot flow into the chamber. Moreover, inside of each port 32 and 33, the guide plate 39 is disposed and arranged so that steam flowing through the port is conducted upwardly and any possible condensate is let off and prevented from entering the chamber 24.

A control valve 40 is arranged in the steam supply conduit which operates by dependence on the pressure in the chamber 26. Moreover, a control means 41 of the valve 40 is connected to a pressure sensor 43 within the space 26 by means of a conduit 42.

According to the invention, sterilization in the autoclave is performed in the following manner: The valve 40 in the supply conduit is inoperative and closed as is the valve 36 and the discharge conduit from the chamber 24. Articles 25 are then placed in the chamber 24 and the autoclave door (not shown) is closed. The valve 30 is then opened and the vacuum pump 31 made operative. Air in the space 26 and the chamber 24 is drawn out and at a given negative pressure in the chamber the control means 41 of the valve 40 is actuated to open so that steam is supplied to the space 26. As stated hereinbefore, the restricted connection between the ports 32 and 33, the space 26, and the chamber 24 provide a free path and thus steam from the space 26 will flow to the chamber 24. The vacuum pump 31 continues drawing a vacuum through the discharge conduit 29 and hence steam will flow toward this point through the space 26, the ports 32 and 33 and also through the chamber 24. However, after a given period of time, the vacuum pump 31 is rendered inoperative and the valve 30 is closed. Moreover, the steam supply continues until the pressure chamber 26 has reached the value set by the sensor 43. Since superatmospheric pressure prevails, a valve 36 and a discharge conduit 34 from the chamber 24 is opened and the throttle 37 and the conduit 34 becomes active and a restricted flow of steam is passed therethrough. When this occurs the pressure in the chamber 24 will be reduced a small amount and steam continues to flow from the space 26 to the chamber 24. Since the pressure in the chamber 26 falls, the sensor 43 will react and open the valve 40 so that the new steam supply is provided for the space. Inasmuch as a constant flow of steam is obtained, it is possible to control temperature and pressure in the chamber so that very small variations from the intended values will occur.

After the sterilization process has been completed, the treatment of the articles in the chamber 24 can be performed in a known manner.

It should be noted that during the period when a vacuum is drawn on the system, steam is caused to flow by the action of the pump, during the heating period by the consumption of steam for heating and condensation of the steam, and during the sterilization period both by heat consumption and by the flow of steam through the throttle 37.

Because of the special design of the connection between the space 26 and the chamber 24 creating a flow resistance a small pressure difference is maintained between the space 26 and chamber 24 during all those periods of treatment when operating with steam in the chamber. This pressure difference makes it possible to use the best flow velocity of the steam being supplied to the chamber without the risk of getting intermittent velocities which are too high. Thus, in accordance with the teachings of the present invention, the flow velocity of the steam between the space 26 and the chamber 24 is adapted so that there will be a minimum of energy losses. Furthermore, the risk is eliminated that steam flow in the connection between the space and the chamber forms a constant source of transfer of condensate from the space to the chamber.

It should be evident that the present invention is not limited to the design of the autoclave operating with steam for sterilization as shown and described but can be modified within the scope of the following claims.

As an alternative, the discharge conduit 34 from the chamber 24 can be replaced by a branch conduit 44 as shown in dashed lines. This branch conduit 44 leads to a common discharge conduit 29. Furthermore, the branch conduit 44 circumvents the valve 30 in the vacuum pump conduit 29 and opens directly into the common drain 35. The branch conduit 44 also, like the conduit 34, includes a throttle 45 and a shut-off valve 46.

What is claimed is:

1. A method of sterilizing articles in an autoclave operating with steam and having a pressure vessel type outer wall and a non-pressure type inner wall, said inner wall defining a chamber for receiving the articles to be sterilized, an outer space between said outer wall and said inner wall, a steam supply conduit to said outer space and an open connection between said outer space and said chamber, said connection consisting of a series of holes provided in said inner wall, said method comprising: passing steam through said connection at approximately the thermodynamic optimum velocity, maintaining a constant pressure difference of 0.01–0.02 atmospheres between said outer space and said chamber when steam is supplied to said autoclave by means of the arrangement and construction of said connection between said outer space and chamber, and discharging a given quantity of steam from said chamber through a conduit provided with a throttle therein.

2. In an autoclave operating with steam for the sterilization of articles having a pressure vessel type outer wall and a non-pressure type inner wall, the latter defining a chamber for treatment of said articles, an outer space between said outer wall and said inner wall, a steam supply conduit connected to said outer space, a relatively short open connection between said outer space and said chamber, the improvement comprising a restricted outlet for said chamber, and the further improvement wherein said connection consists of a series of holes provided in said inner wall and arranged and constructed to cause a given, substantially constant pressure difference of 0.01–0.02 atmospheres between said outer space and said chamber when steam is supplied to said autoclave.

3. The autoclave as claimed in claim 2 further comprising a control valve in said steam supply conduit, a pressure sensor in said outer space and operatively connected to said control valve, and wherein said restricted outlet comprises a discharge conduit having a throttle therein.

4. The autoclave as claimed in claim 2 wherein, given a predetermined velocity of steam flowing through said steam supply conduit, said connection is so arranged and constructed that the steam velocity passing therethrough is between 35 m/s and 60 m/s.

5. The autoclave as claimed in claim 2 wherein said connection is so constructed and arranged that the steam flow therein is subject to at least a 90° change in direction.

6. The autoclave as claimed in claim 2 wherein said connection is provided with means for leading off condensate in said connection to said outer space.

7. The autoclave as claimed in claim 2 wherein opposite edges of the top of said inner wall are bent outwardly to form part of said connection, and to prevent condensate above said connection from flowing therethrough and into said chamber.

* * * * *